(12) United States Patent
Hyzdu

(10) Patent No.: US 9,345,309 B1
(45) Date of Patent: May 24, 2016

(54) INFUSION PUMP TRANSPORT AND HOLDING SYSTEM

(76) Inventor: Julie Hyzdu, Mesa, AZ (US)

( * ) Notice: Subject to any disclaimer, the term of this patent is extended or adjusted under 35 U.S.C. 154(b) by 0 days.

(21) Appl. No.: 12/958,372

(22) Filed: Dec. 1, 2010

Related U.S. Application Data

(60) Provisional application No. 61/265,719, filed on Dec. 1, 2009.

(51) Int. Cl.
*A45F 5/00* (2006.01)

(52) U.S. Cl.
CPC .......................................... *A45F 5/00* (2013.01)

(58) Field of Classification Search
CPC .......................................................... A45F 5/00
USPC .......... 224/219–222, 637, 660; 604/332, 337, 604/345
See application file for complete search history.

(56) References Cited

U.S. PATENT DOCUMENTS

| | | | |
|---|---|---|---|
| 4,087,864 A | 5/1978 | LaBove et al. | |
| 4,578,062 A | 3/1986 | Schneider | |
| 4,579,265 A * | 4/1986 | Schiller | 224/682 |
| 4,582,508 A | 4/1986 | Pavelka | |
| 4,666,432 A | 5/1987 | McNeish et al. | |
| 4,698,848 A | 10/1987 | Buckley | |
| 4,718,124 A | 1/1988 | Sawicki et al. | |
| 4,974,762 A * | 12/1990 | Boretsky et al. | 224/148.5 |
| 5,026,362 A * | 6/1991 | Willett | 604/345 |
| 5,165,115 A | 11/1992 | Stanislaw | |
| 5,403,285 A | 4/1995 | Roberts | |
| 5,418,978 A | 5/1995 | Hochman | |
| 5,425,719 A * | 6/1995 | Lessing, Jr. | 604/179 |
| 5,523,581 A * | 6/1996 | Cadwalader | 250/519.1 |
| 5,611,085 A | 3/1997 | Rasmussen | |
| 5,708,978 A | 1/1998 | Johnsrud | |
| 5,728,070 A | 3/1998 | Walker et al. | |
| 5,755,679 A * | 5/1998 | Selner et al. | 602/27 |
| 5,755,698 A | 5/1998 | Kagan et al. | |
| 5,823,984 A | 10/1998 | Sliverberg | |
| D404,908 S * | 2/1999 | Lollis | D3/215 |
| 5,894,976 A | 4/1999 | Harper | |
| 5,897,519 A | 4/1999 | Shesol et al. | |
| 5,941,856 A | 8/1999 | Kovacs et al. | |
| 6,032,289 A | 3/2000 | Villapiano | |
| 6,055,668 A | 5/2000 | Gros et al. | |
| 6,065,154 A | 5/2000 | Hulings et al. | |
| 6,129,709 A | 10/2000 | Millen | |
| 6,390,885 B1 | 5/2002 | Brooks | |
| 6,461,319 B1 | 10/2002 | Ekey | |
| 6,477,710 B1 | 11/2002 | Ojoyeyi | |
| 6,574,800 B1 | 6/2003 | Leger et al. | |
| 6,676,613 B2 | 1/2004 | Cantrell et al. | |
| 6,681,404 B1 | 1/2004 | Adlard et al. | |
| 6,886,283 B2 * | 5/2005 | Arraut | 40/661 |
| 6,973,673 B2 | 12/2005 | Beuk | |
| 7,364,491 B2 | 4/2008 | Updyke | |
| 7,418,741 B2 | 9/2008 | Rogers | |
| 7,738,965 B2 | 6/2010 | Phillips et al. | |

(Continued)

*Primary Examiner* — Brian D Nash
(74) *Attorney, Agent, or Firm* — Jackson White, PC; Steven J. Laureanti

(57) ABSTRACT

An apparatus is disclosed for strapping around the body of a user comprising one or more pockets to securely hold a device that may be connected to the user. The apparatus includes a band comprising a first side and a second side and a fastening tab attachably connected on a first end of the second side of the band. The apparatus also includes a pocket attachably connected on a first side of the band.

13 Claims, 3 Drawing Sheets

(56) References Cited

U.S. PATENT DOCUMENTS

2005/0020982 A1   1/2005   Shaw
2005/0033241 A1   2/2005   Hottinger
2005/0040194 A1*  2/2005   Frye et al. .................... 224/219
2005/0256466 A1* 11/2005   Winkler ........................ 604/337
2008/0011794 A1*  1/2008   Daniel .................... A45F 5/022
                                                      224/183
2009/0054844 A1   2/2009   Alyea et al.
2009/0179053 A1*  7/2009   Cooney et al. ................ 224/219
2009/0216197 A1   8/2009   Russo
2009/0234296 A1   9/2009   Robison

* cited by examiner

INFUSION PUMP TRANSPORT AND HOLDING SYSTEM

CROSS-REFERENCE TO RELATED APPLICATIONS

The present invention is related to that disclosed in U.S. Provisional Patent Application Ser. No. 61/265,719, filed 1 Dec. 2009, entitled "Device for Holding Chemotherapy Pump." The subject matter disclosed in U.S. Provisional Patent Application Ser. No. 61/265,719 is hereby incorporated by reference into the present disclosure as if fully set forth herein. The present invention hereby claims priority under 35 U.S.C. §119(e) to U.S. Provisional Patent Application Ser. No. 61/265,719.

TECHNICAL FIELD OF THE INVENTION

This invention relates generally to infusion pump transport and holding system, and more particularly to an apparatus for securely holding a device to be connected to a user.

BACKGROUND OF THE INVENTION

In typical practice, a port is inserted into a patient's chest undergoing medical treatment and a tube, which is connected to an infusion pump, may be inserted into the port. A fanny pack is provided with the infusion pump to be worn below the patients' waist. However, the tubes or wires often are snagged or dislodged because they are dangling from the port to the fanny pack. In addition, the dangling tubes or wires are not discrete and anyone who sees them knows that the patient is going though chemotherapy treatment or some other medical treatment. Moreover, at night, the fanny pack with the pump inside is usually placed on the night stand beside the bed and the tubes or wires often become tangled when the patient rolls during sleep or when a pet chews on them. As such, a need currently exists for an improved product that allows a patient to remain active while wearing the infusion pump without snagging the tubes or wires and without being visibly noticable.

SUMMARY OF THE INVENTION

An apparatus includes a band comprising a first side and a second side and a fastening tab attachably connected on a first end of the second side of the band. The apparatus also includes a pocket attachably connected on a first side of the band.

BRIEF DESCRIPTION OF THE DRAWINGS

The novel features believed characteristic of the invention are set forth in the appended claims. However, the invention itself, as well as a preferred mode of use, and further objectives and advantages thereof, will best be understood by reference to the following detailed description when read in conjunction with the accompanying drawings, wherein:

DETAILED DESCRIPTION OF THE INVENTION

Reference will now be made to the following detailed description of the preferred and alternate embodiments of the present invention. Those skilled in the art will recognize that the present invention provides many inventive concepts and novel features, that are merely illustrative, and are not to be construed as restrictive. Accordingly, the specific embodiments discussed herein are given by way of example and do not limit the scope of the present invention.

Embodiments of the present invention provide an apparatus for strapping around the body of a user comprising one or more pockets to securely hold a device that may be connected to a port associated with the user. By completely enclosing the device and associated accessories (i.e., tubes, cables, wires) in the one or more pockets and tightly strapping the apparatus around the user's body, a user may remain active while wearing the device and accessories underneath the user's clothes without snagging the accessories or damaging the device and without being visibly noticable.

Figure 1A:
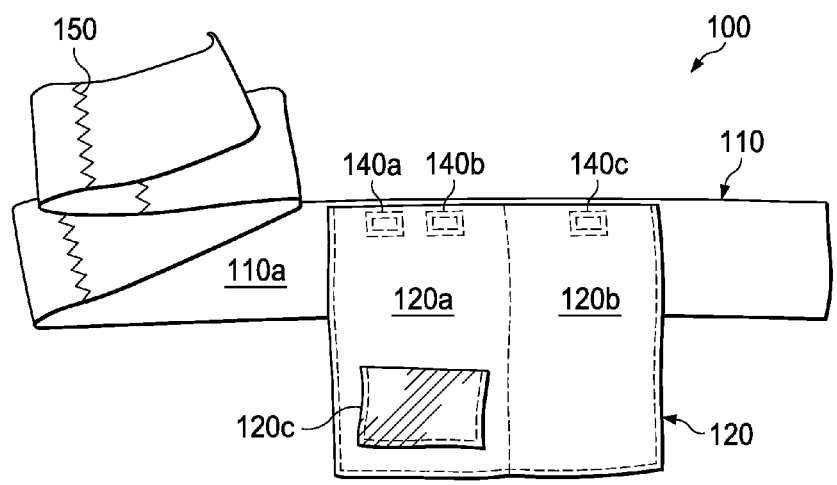
FIGS. 1A and 1B illustrate an exemplary apparatus according to a preferred embodiment.
Figure 1B:
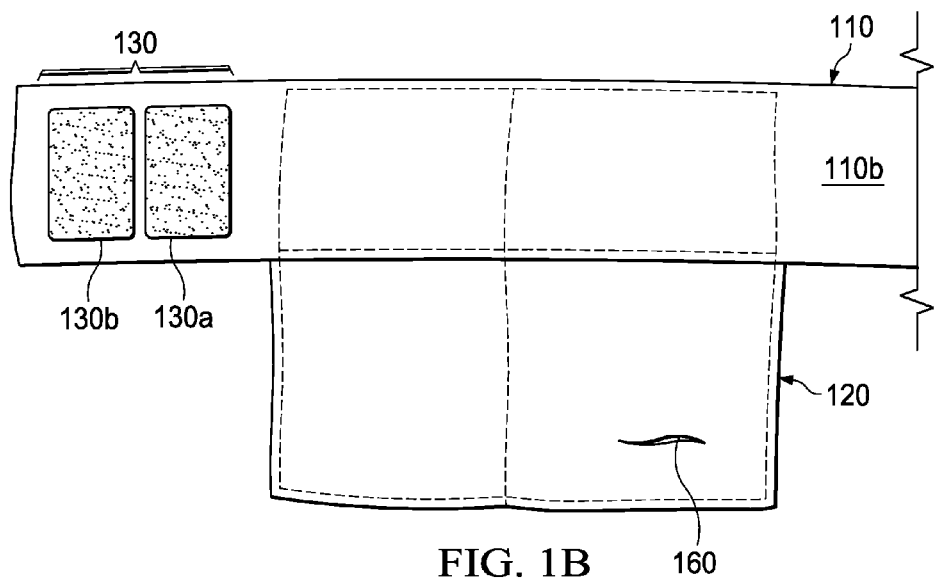

FIGS. 1A and 1B illustrate an exemplary apparatus 100 according to a preferred embodiment. Apparatus 100 comprises a band 110 and a pocket 120. FIG. 1A illustrates a first side 110a of apparatus 100 and FIG. 1B illustrates a second side 110b of apparatus 100. Band 110 comprises a fastening tab 130 on a first end of second side 110b of apparatus 100 (shown in FIG. 1B), which attaches with the second end of second side 110b for securely strapping apparatus 100 around the body of a user. In one embodiment, fastening tab 130 is a hook and pile system, such as VELCRO™ and may be a single tab 130, or two or more tabs 130a and 130b, according to particular needs. In addition, the length of band 110 is substantially longer then the width of band 110 to provide for wrapping around a user's body. In an embodiment, a plurality of zig-zag surge stitches 150 are placed at predetermined intervals and perpendicular to the length of band 110 to allow a user to cleanly cut band 110 and decrease the length of band 110, depending upon the application.

In one embodiment, pocket 120 comprises a device pocket 120a, an accessory pocket 120b, and a clear pocket 120c. These one or more pockets 120 may comprise one or more access holes 160 on the back of the one or more pockets 120 to allow the accessories associated with the device access to the port on the user. In addition, the one or more pockets 120 comprise one or more internal cavities that are externally accessible, such as the internal cavities of pockets 120a, 120b and 120c. Once these one or more internal cavities of pockets 120 are opened and are externally accessible to a user, a device or other object may be is inserted in the one or more pockets 120. Although a single band 110 and a single pocket 120 are shown and described; embodiments contemplate any number of bands 110 or any number of pockets attachably connected with band 110, according to particular needs. In addition, as described below in more detail with reference to FIGS. 2A, 2B, 3A and 3C, various configurations of one or more pockets 120 may be attachably connected with band 110, according to other embodiments.

In one embodiment, band 110 is made out of a stretchable fabric such as LYCRA™, any woven material, spandex, rubber, latex, or other suitable material. For example, band 110 is made from an elastic medical material, such that the first side 110a of band 110 is made of a smooth medical elastic, rubber, or latex while the second side 110b of band 110 is made of a plush hook material. The combination of the plush hook material of the second side of 110b of band 110 with fastening tabs 130 provides for secure attachment of apparatus 100 around a user's body. Among other things, this provides for the stretchability of band 110 around the user's body and the comfort of band 110 against the user's body.

In one embodiment, pocket 120 is stitched to the band 110 and is made of a polyester stretch material, wherein the material may be any material, such as for example, fabric, any color of fabric, and may comprise any pattern on the fabric, according to particular needs. In addition, a clear vinyl may be used for one or more pockets 120, such as clear pocket 120c. Furthermore, although one or more pockets 120 are shown and described as being stitched with band 110, embodiments contemplate taping, binding, gluing, or otherwise affixing pocket 120 with band 110 in any appropriate manner. In another embodiment, some or all of pocket 120 may be affixed to band 110, according to particular needs.

In another embodiment, a user may insert an infusion pump, such as a chemotherapy cancer pump into the internal cavity of device pocket 120a and insert the tubes of the chemotherapy cancer pump into the internal cavity of accessory pocket 120b. In addition, device pocket 120a and accessory pocket 120b comprise tabs 140a, 140b, and 140c having a hook and pile system, such as VELCRO™, tabs to close pockets 120a and 120b in order to enclose and protect the chemotherapy cancer pump and tubes within the internal cavities of pockets 120. Accordingly, the chemotherapy cancer pump may be connected via the tubes into a port in the user's chest, while containing the pump within device pocket 120a and the tubes within accessory pocket 120b.

In addition, or as an alternative, a user may insert a contact card into clear pocket 120c; including a telephone number to call if the chemotherapy cancer pump becomes dislodged or won't stop beeping. Although apparatus 100 has been described in context of holding a chemotherapy cancer pump and associated tubes, other devices may be used, such as, for example, other types of infusion pumps, medical devices, diabetes pumps, music players, wireless devices, food and drinks, or any other device or object. In addition, although a hook and pile system is shown and described with pockets 120; embodiments contemplate using a zipper, snap or other suitable connection system to securely close pockets 120, according to particular needs.

In one embodiment, apparatus 100 may be strapped around the chest of a person directly over the skin or over an undershirt or other closing using band 110. In this manner, the user's clothing over apparatus 100 completely hides apparatus 100 from being seen. In addition, and not by way of limitations, the components of apparatus 100 may be configured to connect band 110 around the chest of a user via the user's left hand instead of the user's right hand. Furthermore, pocket 120 may be placed based upon the location of the port or other connection on the user's chest or body. Band 110 is adjustable and may be moved around a user's chest for each individual user.

In addition, apparatus 100 may be of different sizes. For example, apparatus 100 may be a XS-m size with a band 110 length of 22-40 in, or an L-X×L size with a band 110 length of 38-56 in. In addition, the width of the band 110 may be 4 inches but may be smaller or larger, according to particular needs. Although a particular length and width of band 110 has been shown and described, embodiments contemplate any particular length or width of band 110, according to particular needs.

Figure 2A:
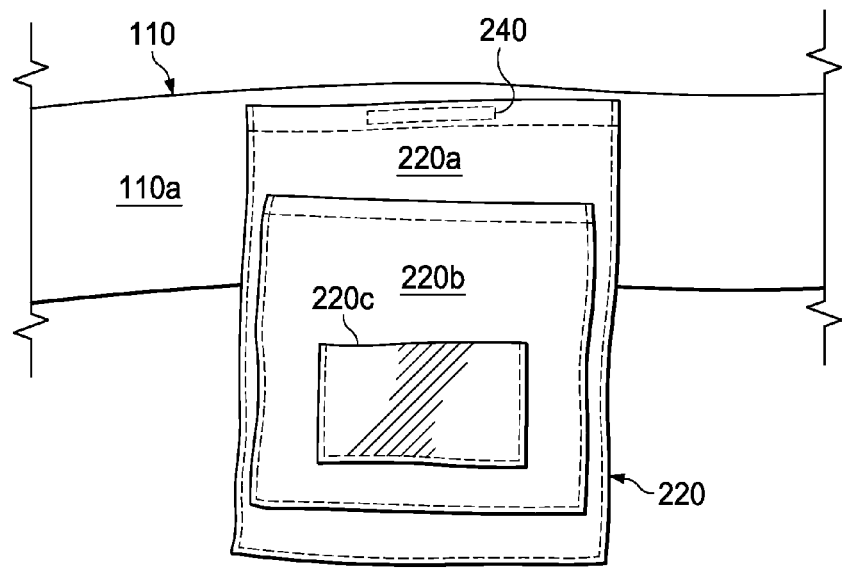
FIGS. 2A and 2B illustrate the apparatus of FIG. 1 in greater detail in accordance with another embodiment.
Figure 2B:
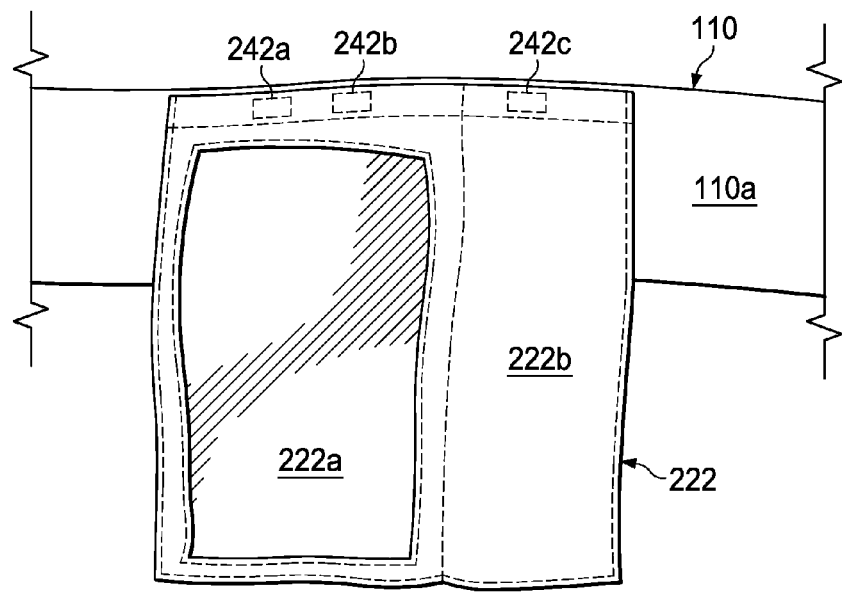

FIGS. 2A and 2B illustrate apparatus 100 of FIG. 1 according to another embodiment. As discussed above, one or more pockets may be stitched, taped, bound, glued, or otherwise affixed to a first side 110a of band 110 in any appropriate manner. FIG. 2A illustrates band 110a of FIG. 1 and a pocket 220. In one embodiment, pocket 220 comprises a device pocket 220a, an accessory pocket 220b, and a clear pocket 220c. In addition, and as discussed above, the one or more pockets comprise one or more internal cavities that are externally accessible, such as the internal cavities of pockets 220a, 220b and 220c. Once these one or more internal cavities of pockets 220 are opened and are externally accessible to a user, a device or other object may be is inserted in the one or more pockets 220. In addition, or as an alternative, clear pocket 220c is affixed on the top side of accessory pocket 220b, which is affixed on the top side of device pocket 220a. In addition, device pocket 220a comprises tab 240 having a hook and pile system, such as VELCRO™, tab to close pockets 220 in order to enclose and protect a device and accessories within the internal cavities of device pocket 220a.

FIG. 2B illustrates band 110a of FIG. 1 and a pocket 222. In one embodiment, pocket 222 comprises a device pocket 222a and an accessory pocket 222b. Furthermore, and as discussed above, the one or more pockets comprise one or more internal cavities that are externally accessible, such as the internal cavities of pockets 222a and 222b. In addition, or as an alternative, device pocket 222a comprises a clear front cover. In addition, device pocket 222a and accessory pocket 222b comprise tabs 242a, 242b, and 242c having a hook and pile system, such as VELCRO™, tabs to close pockets 222a and 222b in order to enclose and protect the device and accessories within the internal cavities of pockets 222.

Figure 3A:
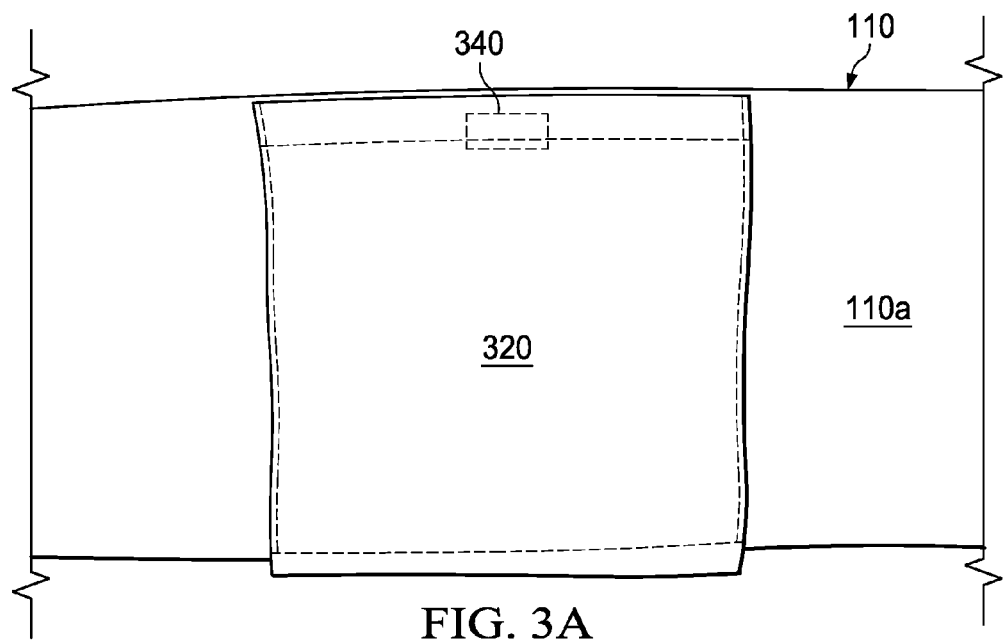
FIGS. 3A and 3B illustrate the apparatus of FIG. 1 in greater detail in accordance with another embodiment.
Figure 3B:
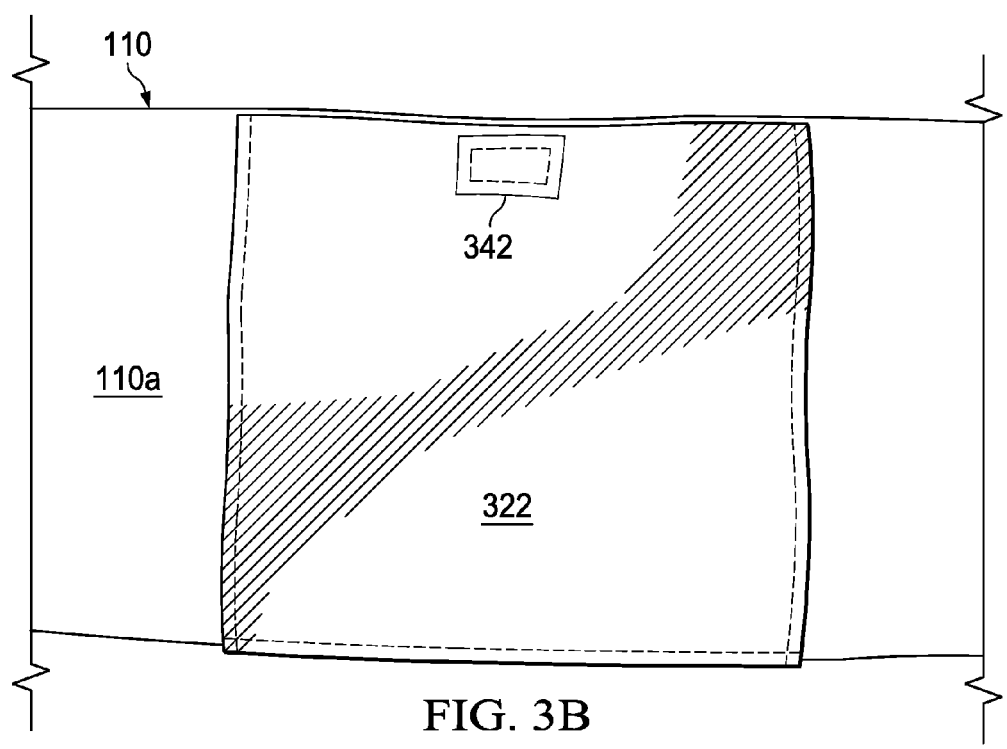

FIGS. 3A and 3B illustrate apparatus 100 of FIG. 1 according to another embodiment. As discussed above, one or more pockets may be stitched, taped, bound, glued, or otherwise affixed to a first side 110a of band 110 in any appropriate manner. FIG. 3A illustrates band 110a of FIG. 1 and a pocket 320. In one embodiment, pocket 320 comprises one or more internal cavities that are externally accessible. Once these one or more internal cavities of pockets 320 are opened and are externally accessible to a user, a device or other object may be is inserted in the one or more internal cavities. In addition, pocket 320 comprises tab 340 having a hook and pile system, such as VELCRO™, tab to close pocket 320 in order to enclose and protect a device and accessories within the one or more internal cavities.

FIG. 3B illustrates band 110a of FIG. 1 and a clear pocket 322 which as discussed above, comprises one or more internal cavities that are externally accessible. In addition, clear pocket 322 comprises tab 342 having a hook and pile system, such as a VELCRO™, tab to close clear pocket 322 in order to enclose and protect the device and accessories within the internal cavities of clear pocket 322.

Reference in the foregoing specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

While the exemplary embodiments of the present invention have been shown and described, it will be understood that various changes and modifications to the foregoing embodiments may become apparent to those skilled in the art without departing from the spirit and scope of embodiments of the present invention. Accordingly, the invention is not limited to the embodiments disclosed, but is capable of numerous rearrangements, modification and substitutions without departing form the spirit and scope of the present invention.

What is claimed is:

1. An apparatus, comprising:
   a band comprising a single fabric of medical grade elastic material comprising a first side of plush material, a second side of smooth medical elastic, a band top portion and a band bottom portion, wherein the band is user-adjustable and comprises a plurality of zig-zag surge stitches perpendicular to the length of the band, configured to allow sizing of the band by cutting the band between adjacent zig-zag surge stitches;

a fastening tab attachably connected on a first end of the second side of the band, the fastening tab configured to attach with the first side of plush material, wherein the band top portion of the second side of the band is horizontally aligned with the band top portion of the first side and the band bottom portion of the second side of the band is horizontally aligned with the band bottom portion of the first side; and a pocket comprising a polyester stretch material and comprising a pocket top portion, a pocket bottom portion, a pocket front surface, a pocket back surface, and a vertical partition forming a first internal cavity and a second internal cavity, the first internal cavity sized larger than the second internal cavity and externally accessible from the pocket top portion, the pocket back surface is attachably connected on the first side of the band, the pocket top portion of the pocket front surface and the pocket back surface horizontally aligned with the band top portion, the pocket bottom portion extending greater than two times the width of the band below the band bottom portion, and one or more tabs disposed on an internal front surface and an internal back surface of the pocket top portion of each internal cavity.

2. The apparatus of claim 1, wherein the pocket is stitched to the band.

3. The apparatus of claim 1, wherein the pocket is further comprised fully or partially of a clear front cover.

4. The apparatus of claim 1, further comprising a clear pocket attachably connected to a front side of the pocket.

5. The apparatus of claim 1, wherein the one or more tabs is a connector selected from the group consisting of a hook and pile system, snaps, buttons, and a zipper.

6. The apparatus of claim 1, wherein the pocket comprises an access hole on the back portion of the pocket.

7. The apparatus of claim 1, wherein the fastening tab comprises two fastening tabs.

8. An apparatus, comprising:
a band comprising a single fabric of medical grade elastic material comprising a first side of plush material, a second side of smooth medical elastic, a band top portion and a band bottom portion, wherein the band is user-adjustable and comprises a plurality of zig-zag surge stitches perpendicular to the length of the band, configured to allow sizing of the band by cutting the band between adjacent zig-zag surge stitches;

a fastening tab attachably connected on a first end of the second side of the band, the fastening tab configured to couple with the first side of plush material, wherein the band top portion of the second side of the band is horizontally aligned with the band top portion of the first side and the band bottom portion of the second side of the band is horizontally aligned with the band bottom portion of the first side; and a pocket comprising polyester stretch material and comprising a pocket top portion, a pocket bottom portion, a pocket front surface, a pocket back surface, and an internal cavity externally accessible from the pocket top portion, the pocket back surface is attachably connected on the first side of the band, the pocket top portion of the pocket front surface and the pocket back surface horizontally aligned with the band top portion, the pocket bottom portion horizontally aligned with the band bottom portion and one or more tabs disposed on an internal front surface and an internal back surface of the pocket top portion of the internal cavity.

9. The apparatus of claim 8, wherein the one or more tabs is a connector selected from the group consisting of a hook and pile system, snaps, buttons, and a zipper.

10. The apparatus of claim 8, wherein the pocket is further comprised of a clear front cover.

11. An apparatus, comprising:
a band comprising a single fabric of medical grade elastic material comprising a first side of plush material, a second side of smooth medical elastic, a band top portion and a band bottom portion, wherein the band is user-adjustable and comprises a plurality of zig-zag surge stitches perpendicular to the length of the band, configured to allow sizing of the band by cutting the band between adjacent zig-zag surge stitches;

a fastening tab attachably connected on a first end of the second side of the band, the fastening tab configured to couple with the first side of plush material, wherein the band top portion of the second side of the band is horizontally aligned with the band top portion of the first side and the band bottom portion of the second side of the band is horizontally aligned with the band bottom portion of the first side;

a first pocket comprising polyester stretch material and comprising a first pocket top portion, a first pocket bottom portion, a first pocket front surface, a first pocket back surface, a first front side and a first internal cavity externally accessible from the first pocket top portion, the first pocket attachably connected on the first side of the band, the first pocket top portion of the first pocket front surface and the first pocket back surface horizontally aligned with the band top portion, the first pocket bottom portion extending greater than two times the width of the band, below the band bottom portion, one or more tabs disposed on an internal front surface and an internal back surface of the first pocket top portion; and a second pocket comprising polyester stretch material and comprising a second pocket top portion, a second pocket bottom portion, a second front side and a second internal cavity externally accessible from the second pocket top portion, the second pocket attachably connected to the first front side of the first pocket.

12. The apparatus of claim 11, wherein the one or more tabs is a connector selected from the group consisting of a hook and pile system, snaps, buttons, and a zipper.

13. The apparatus of claim 11, further comprising a clear pocket is attachably connected to the second front side of the second pocket.

* * * * *